(12) United States Patent
Smith et al.

(10) Patent No.: US 10,724,075 B2
(45) Date of Patent: Jul. 28, 2020

(54) REDUCING DNA DAMAGE DURING SAMPLE PREPARATION AND SEQUENCING USING SIDEROPHORE CHELATORS

(71) Applicant: Illumina Cambridge Limited, Essex (GB)

(72) Inventors: Vincent Peter Smith, Cambridge (GB); Sohela de Rozieres, San Diego, CA (US)

(73) Assignee: Illumina Cambridge Limited, Essex (GB)

( * ) Notice: Subject to any disclaimer, the term of this patent is extended or adjusted under 35 U.S.C. 154(b) by 225 days.

(21) Appl. No.: 15/787,968

(22) Filed: Oct. 19, 2017

(65) Prior Publication Data

US 2018/0051323 A1    Feb. 22, 2018

Related U.S. Application Data

(62) Division of application No. 14/923,319, filed on Oct. 26, 2015, now Pat. No. 9,828,627.

(60) Provisional application No. 62/075,708, filed on Nov. 5, 2014.

(51) Int. Cl.
| | | |
|---|---|---|
| *C12Q 1/6806* | (2018.01) | |
| *C12Q 1/6869* | (2018.01) | |
| *C12N 15/10* | (2006.01) | |

(52) U.S. Cl.
CPC ........ *C12Q 1/6806* (2013.01); *C12N 15/1093* (2013.01); *C12Q 1/6869* (2013.01)

(58) Field of Classification Search
CPC .................................................. C12Q 1/6806
USPC ......................................................... 506/30
See application file for complete search history.

(56) References Cited

U.S. PATENT DOCUMENTS

| | | |
|---|---|---|
| 8,841,075 B1 | 9/2014 | Borner et al. |
| 2004/0146964 A1 | 7/2004 | Maxwell et al. |
| 2008/0131876 A1 | 6/2008 | Hantash |
| 2008/0287548 A1* | 11/2008 | Anziano ............... C07C 235/32 514/622 |
| 2009/0246763 A1 | 10/2009 | Eason |
| 2010/0111856 A1 | 5/2010 | Gill et al. |
| 2011/0111969 A1 | 5/2011 | Chintalgiri et al. |
| 2012/0183531 A1 | 7/2012 | Lucas et al. |
| 2013/0183679 A1 | 7/2013 | Ploy et al. |
| 2015/0019189 A1* | 1/2015 | Matson ................ G16B 40/00 703/11 |
| 2015/0056609 A1 | 2/2015 | Daum et al. |
| 2016/0024559 A1 | 1/2016 | Sangha et al. |
| 2016/0184244 A1 | 6/2016 | Nicolls et al. |

FOREIGN PATENT DOCUMENTS

| | | |
|---|---|---|
| EP | 0 747 488 A1 | 12/1996 |
| WO | WO 00/01850 A2 | 1/2000 |
| WO | WO 2014/108810 A2 | 7/2014 |

OTHER PUBLICATIONS

Costello et al. (Nucleic Acids Research, published online Jan. 8, 2013, vol. 41, No. 6, pp. 1-12) (Year: 2013).*
Hider, Robert C., et al: "Chemistry and biology of siderophores", *Natural Product Reports*, vol. 27, No. 5, (2010), p. 637.
Kanvah, Sriram, et al: "Oxidation of DNA: Damage to Nucleobases", *Accounts of Chemical Research.*, vol. 43, No. 2, (2010), pp. 280-287.
Lloyd, Daniel R., et al: "Oxidative DNA damage mediated by copper(II), iron(II) and nickel(II) Fenton reactions: evidence for site-specific mechanisms in the formation of double-strand breaks, 8-hydroxydeoxyguanosine and putative intrastrand cross-links", *Mutation Research*, vol. 424, No. 1-2, (1999), pp. 23-36.
Son, Mike S., et al., "Preparing DNA Libraries for Multiplexed Paired-End Deep Sequencing for Illumina GA Sequencers," *Current Protocols in Microbiology*, Feb. 1, 2011.
Wang, W., et al: "Real-time detection of Fe{middle dot}EDTA/H2O2-induced DNA cleavage by linear dichroism", *Nucleic Acids Research*, vol. 36, No. 14, (2008), pp. e85-e85.
International Search Report and Written Opinion for PCT/US2015/057409 dated Apr. 7, 2016.

\* cited by examiner

*Primary Examiner* — Karla A Dines
(74) *Attorney, Agent, or Firm* — Knobbe, Martens, Olson & Bear LLP (57) ABSTRACT

Embodiments disclosed herein provide reagents and kits for nucleic acid preparation comprising a siderophore. Embodiments disclosed herein provide methods for preparing a nucleic acid library, which comprise: providing a plurality of nucleic acid molecules from a sample; and manipulating the plurality of nucleic acid molecules in a reagent for nucleic acid preparation comprising a siderophore. Further, embodiments disclosed herein provide methods for reducing oxidative damage to a nucleic acid molecule or increasing the Q (phred) score of a sequencing reaction, which methods comprise preparing the nucleic acid molecule in the absence of EDTA.

20 Claims, 1 Drawing Sheet

REDUCING DNA DAMAGE DURING SAMPLE PREPARATION AND SEQUENCING USING SIDEROPHORE CHELATORS

PRIORITY

This application is a division of U.S. Ser. No. 14/923,319 filed Oct. 26, 2015 which claims priority to U.S. Provisional App. No. 62/075,708 filed Nov. 5, 2014, which are each incorporated herein by reference in its entirety for all purposes.

FIELD

Embodiments provided herein relate to methods and compositions for next generation sequencing. Some embodiments relate to reagents for sequencing-related sample preparation comprising a siderophore and an electrolyte.

BACKGROUND

Chelating agents are used in biochemistry to remove or inactivate divalent cations that can lead to deleterious and unwanted effects in the reaction. The current use of EDTA as a chelator in sequencing related sample preparation applications can lead to severe and irreversible oxidation of the DNA especially in the presence of contaminating iron, due to the generation of an $Fe^{2+}$(EDTA) complex which promotes damaging free-radical chemistry (Lloyd and Phillips, *Mutation Res.* (1999) 424:23-36; Wang et al., *Nuc. Acid Res.* (2008) 36:e85). This results in local point mutations in the DNA sample leading to erroneous polymorphism calls during deep sequencing analysis. This phenotype is especially problematic in cancer-related deep sequencing applications where low frequency polymorphisms must be detected sensitively and are of great biological significance.

SUMMARY OF EMBODIMENTS OF THE INVENTION

Embodiments disclosed herein provide reagents for nucleic acid preparation comprising a siderophore. In some embodiments, the siderophore is a bacterial siderophore. In some embodiments, the siderophore is a desferrioxamine B (DFO-B) mesylate salt. In some embodiments, the reagents may comprise a DNA polymerase. In some embodiments, the reagents may comprise dNTPs. In some embodiments, the reagents do not contain EDTA.

Embodiments disclosed herein provide methods for preparing a nucleic acid library, which comprise: providing a plurality of nucleic acid molecules from a sample; and manipulating the plurality of nucleic acid molecules in a reagent for nucleic acid preparation comprising a siderophore. In some embodiments, manipulating the plurality of nucleic acid molecules comprises hybridizing the plurality of nucleic acid molecules to a plurality of oligonucleotide probes. In some embodiments, the plurality of nucleic acid molecules and/or the plurality of oligonucleotide probes are immobilized on a support. In some embodiments, the plurality of nucleic acid molecules and/or the plurality of oligonucleotide probes are immobilized on the support through a binding partner pair to the support. In some embodiments, the support is a magnetic bead. In some embodiments, manipulating the plurality of nucleic acid molecules comprises removing oligonucleotide probes not specifically bound to the plurality of nucleic acid molecules. In some embodiments, the methods comprise modifying the oligonucleotide probes specifically bound to the plurality of nucleic acid molecules. In some embodiments, the methods comprise fragmenting the plurality of nucleic acid molecules. In some embodiments, the methods comprise adding adapters to the plurality of nucleic acid molecules. In some embodiments, the adapters are added to the plurality of nucleic acid molecules by amplification.

Embodiments disclosed herein provide methods for reducing oxidative damage to a nucleic acid molecule, which methods comprise preparing the nucleic acid molecule in the absence of EDTA. In some embodiments, preparing the nucleic acid molecule comprises preparing the nucleic acid molecule in the presence of a siderophore. In some embodiments, the siderophore is a bacterial siderophore. In some embodiments, the siderophore is a desferrioxamine B (DFO-B) mesylate salt. In some embodiments, preparing the nucleic acid molecule comprises exposing the nucleic acid molecule to Fe(III). In some embodiments, preparing the nucleic acid molecule comprises exposing the nucleic acid molecule to a magnetic bead. In some embodiments, the oxidative damage comprises a point mutation in the nucleic acid molecule. In some embodiments, the point mutation is a C to A transversion.

Embodiments disclosed herein provide methods for increasing the Q (phred) score of a sequencing reaction, which methods comprise preparing a nucleic acid molecule in the absence of EDTA. In some embodiments, preparing the nucleic acid molecule comprises preparing the nucleic acid molecule in the presence of a siderophore. In some embodiments, the siderophore is a bacterial siderophore. In some embodiments, the siderophore is a desferrioxamine B (DFO-B) mesylate salt. In some embodiments, the Q score is greater than about 34. In some embodiments, the Q score is greater than about 38. In some embodiments, the Q score is greater than about 42. In some embodiments, the sequencing reaction is a deep sequencing application. In some embodiments, the deep sequencing application is cancer-related deep sequencing application. In some embodiments, the methods comprise sequencing the nucleic acid molecule in the absence of EDTA.

Embodiments disclosed herein provide kits comprising at least one container means, wherein the at least one container means comprises a reagent for nucleic acid preparation comprising a siderophore. In some embodiments, the siderophore is a desferrioxamine B (DFO-B) mesylate salt. In some embodiments, the reagent does not contain EDTA.

DETAILED DESCRIPTION OF EMBODIMENTS OF THE INVENTION

Definitions

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the singular forms "a", "an", and "the" include plural references unless indicated otherwise, expressly or by context. For example, "a" dimer includes one or more dimers, unless indicated otherwise, expressly or by context.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nornucleotidic backbones, for example, polyamide (e.g., peptide nucleic acids ("PNAs")) and polymorpholino (commercially available from the Anti-Virals, Inc., Corvallis, Oreg., as) NeuGene®) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g., nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

"Nucleic acid probe" and "probe" are used interchangeably and refer to a structure comprising a polynucleotide, as defined above, that contains a nucleic acid sequence that can hybridize to a corresponding target. The polynucleotide regions of probes may be composed of DNA, and/or RNA, and/or synthetic nucleotide analogs.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% complementarity, including for example at least any of 70%, 75%, 80%, 85%, 90%, 95%, 99% or 100% complementarity.

Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C.

Low stringency hybridization refers to conditions equivalent to hybridization in 10% formamide, 5×Denhardt's solution, 6× SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20× SSPE (sodium chloride, sodium phosphate, ethylene diamide tetraacetic acid (EDTA)) contains 3 M sodium chloride, 0.2 M sodium phosphate, and 0.025 M (EDTA). Other suitable moderate stringency and high stringency hybridization buffers and conditions are well known to those of skill in the art.

As used herein, "biological sample" refers to any sample obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. Also included are soil and water samples and other environmental samples, viruses, bacteria, fungi, algae, protozoa and components thereof.

As used herein, the term "specifically binds" refers to the binding specificity of a specific binding pair. Recognition by an antibody of a particular target in the presence of other potential targets is one characteristic of such binding. Specific binding involves two different molecules wherein one of the molecules specifically binds with the second molecule through chemical or physical means. The two molecules are related in the sense that their binding with each other is such that they are capable of distinguishing their binding partner from other assay constituents having similar characteristics. The members of the binding component pair are referred to as ligand and receptor (anti-ligand), specific binding pair (SBP) member and SBP partner, and the like. A molecule may also be an SBP member for an aggregation of molecules; for example an antibody raised against an immune complex of a second antibody and its corresponding antigen may be considered to be an SBP member for the immune complex.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Reagents for Nucleic Acid Preparation

Some embodiments disclosed herein provide reagents for nucleic acid preparation comprising a siderophore, or an analogue thereof.

Siderophores are compounds produced by bacteria, fungi and graminaceous plants that have been known to possess a high affinity and selectivity for Fe(III). See, e.g., Hider & Kong, *Nat. Prod. Rep.* (2010) 27:637-57 for a review of the chemistry and biology of siderophores, the content of which is hereby incorporated by reference in its entirety. Siderophores are low-molecular-weight compounds (500-1500 daltons) possessing a high affinity and selectivity for Fe(III). The biosynthesis of siderophores is typically regulated by the iron levels of the environment where the organism is located. There are over 500 different siderophores, of which 270 have been structurally characterized.

Contemplated by this disclosure are siderophores or analogues thereof that are naturally produced, or are synthesized.

As outlined herein, a variety of siderophores, or analogues thereof, may be suitable for the reagents for nucleic acid preparation disclosed herein. In some embodiments, the siderophore may be a bacterial siderophore, a fungal siderophore, a plant siderophore, or a combination thereof. Siderophores having a variety of functional groups, such as catecholate, α-hydroxycarboxylate, hydroxyphenyloxazolone, hydroxamate, α-aminocarboxylate, α-hydroxyimidazole, etc., or a combination thereof, are contemplated by the instant disclosure. For example, in some embodiments, the siderophore may be a hydroxamate siderophore, such as desferrioxamine B (deferoxamine), desferrioxamine E, fusarinine C, ornibactin, rhodotorulic acid, etc., a catecholate siderophore, such as enterobactin, bacillibactin, vibriobactin, etc., or a mixed ligand, such as azotobactin, pyoverdine, yersiniabactin, etc., or an analogue or combination thereof. Other siderophores that may be used for the reagents include, but are not limited to, mycobactin, ferrichrome, coprogen, arthrob actin, ferrichrome A, 2,3-dihydroxybenzoylserine, avenic acid, rhizoferrin, MECAM, amonabactin T, rhizoferrin, etc., or an analogue or combination thereof. In some embodiments, the siderophore may be desferrioxamine B, or an analogue thereof. In some embodiments, the siderophore may be a desferrioxamine B mesylate salt.

Siderophores with high affinity for Fe(III) are desirable for the methods and compositions disclosed herein. Table 2 of Hider & Kong, supra, lists the Fe(III) affinity constants of some siderophores. Therefore, in some embodiments, the siderophore may have a log $K_f(Fe^{III})$ that is, is about, or is more than, 25, 26, 27, 28, 29, 30, 31, 32, 33, 34, 35, 36, 37, 38, 39, 40, 41, 42, 43, 44, 45, 46, 47, 48, 49, 50, or a log $K_f(Fe^{III})$ that is a range between any of these values, for example, 25 to 50, 30 to 40, 40 to 50, etc.

In some embodiments, the reagents for nucleic acid preparation may have an EDTA concentration that is less than 2 mM, 1 mM, 0.5 mM, 0.2 mM, 0.1 mM, 0.05 mM, 0.02 mM, 0.01 mM, or an EDTA concentration that is a range between any of these values, for example, 0.01 mM to 0.05 mM, 0.02 mM to 0.05 mM, etc. In some embodiments, the reagents for nucleic acid preparation may have an EDTA concentration that is about 0.

Other chelators, such as a siderophore, or an analogue thereof, EGTA, DTPA, etc., may be present in the reagents for nucleic acid preparation in a variety of concentrations. For example, in some embodiments, the reagents for nucleic acid preparation may have a concentration of a siderophore, or an analogue thereof, that is, is about, or is more than 0.01 mM, 0.02 mM, 0.05 mM, 0.1 mM, 0.2 mM, 0.5 mM, 1 mM, or a concentration of a siderophore, or an analogue thereof, that is a range between any of these values, for example, 0.01 mM to 0.05 mM, 0.02 mM to 0.5 mM, etc. In some embodiments, the reagents for nucleic acid preparation may have a concentration of EGTA that is, is about, or is more than 0.01 mM, 0.02 mM, 0.05 mM, 0.1 mM, 0.2 mM, 0.5 mM, 1 mM, or a concentration of EGTA that is a range between any of these values, for example, 0.01 mM to 0.05 mM, 0.02 mM to 0.5 mM, etc. In some embodiments, the reagents for nucleic acid preparation may have a concentration of DTPA that is, is about, or is more than 0.01 mM, 0.02 mM, 0.05 mM, 0.1 mM, 0.2 mM, 0.5 mM, 1 mM, or a concentration of DTPA that is a range between any of these values, for example, 0.01 mM to 0.05 mM, 0.02 mM to 0.5 mM, etc.

Another desirable characteristics for the siderophores is the ability to reduce the generation of reactive oxygen species and/or free radicals in the presence of $Fe^{2+}$.

The methods and compositions disclosed herein may be used in a variety of nucleic acid applications, for example, hybridization, amplification, ligation, extension, washing, sequencing, etc. Common reagents are described in TruSeq® Enrichment Guide, Nextera® Enrichment Sample Preparation Guide, Nextera® Rapid Capture Enrichment Guide, TruSight™ Enrichment Sample Preparation Guide, MiSeq® Reagent Kit v3 Reagent Preparation Guide, HiSeq® Cluster Kit v4 Reference Guide, HiSeq® SBS Kit v4 Reference Guide, NextSeq® 500 System User Guide, TruSeq™ RNA Sample Preparation v2 Guide, Nextera XT DNA Library Preparation Guide, Nextera Mate Pair Sample Preparation Guide, TruSeq Nano DNA Sample Preparation Guide, TruSeq® Small RNA Sample Preparation Guide, TruSeq® Stranded mRNA Sample Preparation Guide, TruSeq® Stranded Total RNA Sample Preparation Guide, TruSeq® RNA Access Library Prep Guide, etc. (Illumina®, Inc., San Diego Calif.), which is incorporated by reference herein in its entirety. However, the reagents listed are modified to reduce or exclude any EDTA, and to include EGTA, DTPA, a siderophore, an analogue thereof, or a combination thereof, as described herein.

Common reagents and/or ingredients include one or more of the following: Resuspension Buffer (RSB), Nestera® Capture Target Buffer 1 (NCT1), Elute Target Buffer 1 (ET1), Elute Target Buffer 2 (ET2), Enrichment Hybridization Buffer (EHB), Enrichment Elution Buffer 1 (EE1), enrichment Wash Solution (EWS), Wash Solution 1 (WS1), Wash Solution 2 (WS2), Wash Solution 3 (WS3), PCR Master Mix (TC #-PMM), Nextera® Enrichment Amplification Mix (NEM), Nextera® Library Amplification Mix (NLM), HT1 Hybridisation buffer, HT2 Wash Buffer, PR1 Wash Buffer, PR2 Wash Buffer, PR3 Wash Buffer, SB1 Wash Buffer, SB2 Wash Buffer, SB3 Wash Buffer, USM Universal Scan Mix, SRE Scan Reagent, SRM Scan Reagent, BB2 Wash Buffer, BB3 Wash Buffer, BB4 Wash Buffer, LNW1 (Library Normalization Wash 1), LNS1 (Library Normalization Storage Buffer 1), RSB (Resuspension Buffer), BWB (Bead Wash Buffer), EPM Enhanced PCR Mix, ELB Elution Buffer, etc. (Illumina®, Inc., San Diego Calif.).

The siderophores, or analogues thereof, disclosed herein may be used with a variety of salts or enzymes. For example, the siderophores, or analogues thereof, disclosed herein should be compatible with most if not all of sequencing and/or library prep reagents, and any enzyme that does not require iron for function.

In some embodiments, the reagents disclosed herein may comprise a DNA polymerase. In some embodiments, the reagents disclosed herein may comprise dNTPs. Other reagents include reagents common in nucleic acid applications, such as sample preparation and/or sequencing.

Methods for Preparing a Nucleic Acid Library

Some embodiments provide methods for preparing a nucleic acid library using the reagents disclosed herein, which comprise: providing a plurality of nucleic acid molecules from a sample; and manipulating the plurality of nucleic acid molecules in the reagent.

In some embodiments, manipulating the plurality of nucleic acid molecules comprises hybridizing the plurality of nucleic acid molecules to a plurality of oligonucleotide probes. In some embodiments, manipulating the plurality of nucleic acid molecules comprises removing oligonucleotide probes not specifically bound to the plurality of nucleic acid molecules.

In some embodiments provided herein, a population of nucleic acids is selectively sheared, single-stranded species and overhangs are removed from the population of nucleic acids, and nucleic acids are repaired. In some embodiments, a population of nucleic acids can be processed by performing two or more of selective shearing, single stranded species removal, nucleic acid overhang removal and nucleic acid repair prior to library preparation. Some such embodiments can provide a substrate for further nucleic acid library preparation. Methods of preparing a nucleic acid library are well known in the art. Examples include ligating adaptors to the nucleic acids in a population of nucleic acids. In some embodiments, nucleic acid fragments can be blunt-ended, phosphorylated, coupled to A-tails, and/or coupled to adaptors to yield a nucleic acid library. In some embodiments, the nucleic acid library may be further amplified. Examples of library preparation protocols include, but are not limited to, methods for Nextera™ DNA Sample Prep Kit (Epicentre® Biotechnologies, Madison Wis.), GL FLX Titanium Library Preparation Kit (454 Life Sciences, Branford Conn.), and the like. The sample as described herein can be further amplified for sequencing or microarray assays by, for example, multiple strand displacement amplification (MDA) techniques. For sequencing after MDA, an amplified sample library is, for example, prepared by creating a DNA library as described in Mate Pair Library Prep kit, Genomic DNA Sample Prep kits or TruSeq™ Sample Preparation or Exome Enrichment kits (Illumina®, Inc., San Diego Calif.). Another useful method for amplifying nucleic acids is rolling circle amplification (RCA), for example, as described in Lizardi et al., Nat. Genet. (1998) 19:225-232 and US 2007/0099208, each of which is incorporated herein by reference in its entirety. Emulsion PCR methods are also useful, exemplary methods which are described in Dressman et al., Proc. Natl. Acad. Sci. USA (2003) 100:8817-8822, WO 05/010145, or U.S. Patent Publ. Nos. 2005/0130173 or 2005/0064460, each of which is incorporated herein by reference in its entirety. Methods of the present disclosure are not limited by any particular library preparation or amplification method.

In some embodiments, the plurality of nucleic acid molecules and/or the plurality of oligonucleotide probes are immobilized on a support. The plurality of nucleic acid molecules or oligonucleotide probes may be immobilized on a support in a number of ways. In some embodiments, purification tags are used. By "purification tag" herein is meant a moiety which can be used to purify a nucleic acid molecule, usually via attachment to a solid support as outlined herein. Suitable purification tags include members of binding partner pairs. For example, the tag may be a hapten or antigen, which will bind its binding partner. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful.

In some embodiments, the plurality of nucleic acid molecules and/or the plurality of oligonucleotide probes are immobilized on the support through a binding partner pair to the support. In some embodiments, the support is a magnetic bead.

In some embodiments, the methods disclosed herein comprise modifying the oligonucleotide probes specifically bound to the plurality of nucleic acid molecules. In some embodiments, the methods disclosed herein comprise fragmenting the plurality of nucleic acid molecules. In some embodiments, adding adapters to the plurality of nucleic acid molecules. In some embodiments, the adapters are added to the plurality of nucleic acid molecules by amplification.

Methods for Reducing Oxidative Damage to a DNA Molecule

Some embodiments disclosed herein provide methods for reducing oxidative damage to a nucleic acid molecule, which comprise preparing the nucleic acid molecule in the absence of EDTA, more preferably in the absence of $Fe^{2+}$ (EDTA).

Using a chelator other than EDTA, or without using a chelator, may be desirable for the methods and compositions disclosed herein. In some embodiments, preparing the nucleic acid molecule comprises preparing the nucleic acid molecule in the presence of EGTA, DTPA, a siderophore, or a combination thereof. In some embodiments, preparing the nucleic acid molecule comprises preparing the nucleic acid molecule in the presence of a siderophore. In some embodiments, the siderophore is a bacterial siderophore. In some embodiments, the siderophore is desferrioxamine B (DFO-B) mesylate salt, or an analogue thereof.

The methods and compositions disclosed herein are useful for reducing reactive oxygen species (ROS) and/or free radicals during preparation of the nucleic acid molecule. For example, in some embodiments, preparing the nucleic acid molecule comprises exposing the nucleic acid molecule to Fe(III). In some embodiments, preparing the nucleic acid molecule comprises exposing the nucleic acid molecule to a magnetic bead. By preparing the sample in the absence of EDTA, and/or including EGTA, DTPA, a siderophore, or a combination thereof, ROS can be reduced.

ROS are generated from normal oxygen metabolism in cells and are recognized as a list of active molecules, such as superoxide; hydrogen peroxide; hydroxyl radical; hydroxyl ion; nitric oxide, etc. ROS are known to cause oxidative damages in nucleic acid molecules. Among all the lesions discovered thus far, one of the most abundant in DNA and RNA is the 8-oxoguanine. See Kasai et al., *Nucleic Acids Res*. (1984) 12:2127-2136; Kasai & Nishimura, *Environ Health Perspect*. (1986) 67:111-116; Kanvah et al., *Acc. Chem. Res*. (2010) 43(2):280-287, the content of each is hereby incorporated by reference in its entirety. Therefore, in some embodiments, the oxidative damage comprises a point mutation in the nucleic acid molecule. As used herein, the term "point mutation" refers to a substitution, a deletion, or an insertion, of one nucleotide or more. In some embodiments, the point mutation is a C to A transversion. By reducing ROS, oxidative damage to nucleic acids can be reduced.

Some of the methods and compositions provided herein include preparing libraries from nucleic acids obtained from samples. As used herein "sample" includes a variety of sources and compositions that contain nucleic acids. The sample may be a biological sample but the term also includes other, e.g. artificial samples which comprise nucleic acids such as PCR products or compositions comprising already purified nucleic acids which may be further concentrated and/or further purified. Biological samples include viral particles, cells, tissues, organs, and any portion of an organism.

In some embodiments of the methods and compositions provided herein, nucleic acids in a population of nucleic acids for preparing a nucleic acid library are repaired. For example, nicks may be filled-in and repaired; overhangs may be copied to form double-stranded segments of a nucleic acid. Methods to repair nucleic acids are well known in the art. In some embodiments, repairing nucleic acids can include excision of modified or damaged bases, removal of abasic sites, fill-in of nicks, ligation of nicks ligation, removal of 3' blocking groups, and reversal of crosslinks such as pyrimidine dimers.

Methods for Increasing the Q Score of a Sequencing Reaction

Some embodiments disclosed herein provide methods for increasing the Q (Phred quality) score of a sequencing reaction, which method comprises preparing a nucleic acid molecule in the absence of EDTA. The Q score was originally developed by the program Phred, and is defined as a property which is logarithmically related to the base-calling error probabilities P: $Q=-10 \log_{10}P$. For example, if Phred assigns a quality score of 30 to a base, the chances that this base is called incorrectly are 1 in 1000.

The Q score of a sequencing reaction may be optimized using the methods and compositions disclosed herein. For example, the sequencing reaction may have a Q score that is, is about, or is more than, 30, 31, 32, 33, 34, 35, 36, 37, 38, 39, 40, 41, 42, 43, 44, 45, 46, 47, 48, 49, 50, or a Q score that is a range between any of these values, for example, 30 to 50, 30 to 40, 40 to 50, 44 to 46, etc. In some embodiments, the Q score is greater than about 34. In some embodiments, the Q score is greater than about 38. In some embodiments, the Q score is greater than about 42.

The methods and compositions disclosed herein are especially useful for deep sequencing reactions. As used herein, "deep sequencing" refers to a sequencing reaction during which the total number of reads is many times larger than the length of the sequence under study. Depth (coverage) is used to refer to the average reads representing a given nucleotide in the reconstructed sequence. Depth can be calculated from the length of the original genome (G), the number of reads (N), and the average read length(L) as N×L/G. Accordingly, deep sequencing means that the depth of the sequencing reaction is greater than 7. For example, a given nucleotide may be covered for a depth that is, is about, or is more than, 30, 31, 32, 33, 34, 35, 36, 37, 38, 39, 40, 41, 42, 43, 44, 45, 46, 47, 48, 49, 50, or a depth that is a range between any of these values, for example, 30 to 50, 30 to 40, 40 to 50, 44 to 46, etc. In some embodiments, the methods disclosed herein may be used for ultra-deep sequencing, which has a sequencing depth of >100 (Ajay et al., *Genome Res.* (2011) 21:1498-505). In some embodiments, the deep sequencing application is cancer-related deep sequencing application. In some embodiments, the methods comprise sequencing the nucleic acid molecule in the absence of EDTA and/or in the presence of EGTA, DTPA, a siderophore, or a combination thereof, as disclosed herein.

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

"Sequencing-by-synthesis ("SBS") techniques" generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in International Patent Pub. No. WO 04/018497 and U.S. Pat. No. 7,057,026, the disclosures of which are incorporated herein by reference in their entireties. This approach is being commercialized by Solexa (now Illumina Inc.), and is also described in International Patent Pub. No. WO 91/06678 and International Patent Pub. No. WO 07/123,744, the disclosures of which are incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference in its entirety). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Pub. No. 2007/0166705, U.S. Patent Pub. No. 2006/0188901, U.S. Pat. No. 7,057,026, U.S. Patent Pub. No. 2006/0240439, U.S. U.S. Patent Pub. No. 2006/0281109, International Patent Pub. No. WO 05/065814, U.S. Patent Pub. No. 2005/0100900, International Patent Pub. No. WO 06/064199, International Patent Pub. No. WO 07/010,251, U.S. U.S. Patent Pub. No. 2012/0270305 and U.S. Patent Pub. No. 2013/0260372, the disclosures of each of which are incorporated herein by reference in its entirety.

Some embodiments can utilize detection of four different nucleotides using fewer than four different labels. For example, SBS can be performed utilizing methods and systems described in U.S. Patent Pub. No. 2013/0079232, which is incorporated herein by reference in its entirety. As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated disclosure of U.S. Patent Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation (SBL) techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBL systems and methods which can be utilized with the methods and systems described herein are described in U.S. Pat. No. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference in its entirety) or nucleotide incorporations can be detected with zero-mode waveguides as described, for example, in U.S. Pat. No. 7,315,019 (which is incorporated herein by reference in its entirety) and using fluorescent nucleotide analogs and engineered polymerases as described, for example, in U.S. Pat. No. 7,405,281 and U.S. Patent Pub. No. 2008/0108082 (each of which is incorporated herein by reference in its entirety). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Patent Pub. No. 2009/0026082; U.S. Patent Pub. No. 2009/0127589; U.S. Patent Pub. No. 2010/0137143; or U.S. Patent Pub. No. 2010/0282617, each of which is incorporated herein by reference in its entirety. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature.

Multiple copies can be produced by amplification methods such as, bridge amplification or emulsion PCR as described in further detail below.

The methods set forth herein can use arrays having features at a density that is, is about, is less than, or is more than, 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or a density that is a range between any of these values, for example, 10 features/cm$^2$ to 5,000,000 features/cm$^2$, 100 features/cm$^2$ to 1,000,000 features/cm$^2$, 500 features/cm$^2$ to 100,000 features/cm$^2$, 1,000 features/cm$^2$ to 50,000 features/cm$^2$, 5,000 features/cm$^2$ to 10,000 features/cm$^2$, etc.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Patent Pub. No. 2010/0111768 A1 and U.S. patent application Ser. No. 13/273,666, each of which is incorporated herein by reference in its entirety. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. patent application Ser. No. 13/273,666, which is incorporated herein by reference in its entirety.

Kits

Embodiments disclosed herein further provide kits comprising at least one container means, wherein the at least one container means comprises a reagent for nucleic acid preparation comprising EGTA, DTPA, a siderophore, or a combination thereof as disclosed herein. In some embodiments, the siderophore is a desferrioxamine B mesylate salt. In some embodiments, the reagents do not include EDTA.

EXAMPLES

The following examples are offered to illustrate but not to limit the invention.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Figure 1:
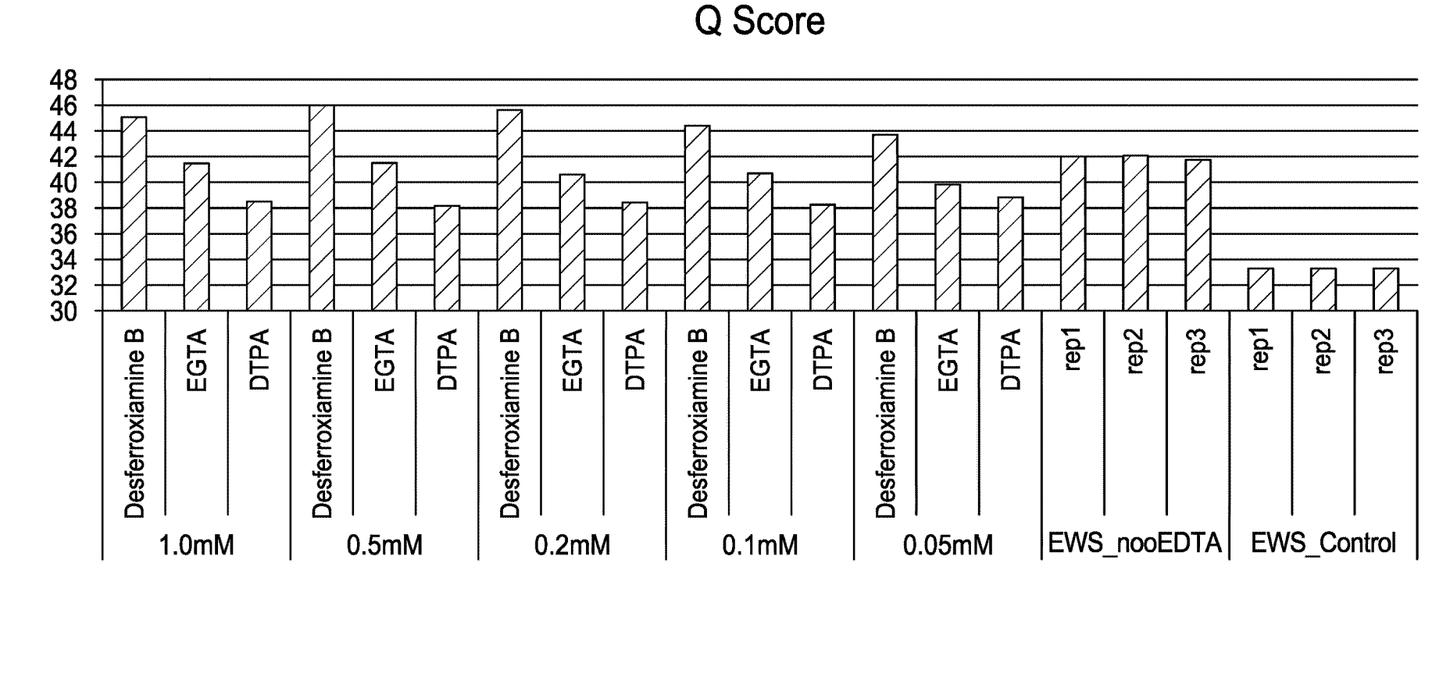
FIG. 1 shows results from an exemplary embodiment of a comparative study of Q scores from sequencing experiments using a buffer with and without EDTA, DFO-B, EGTA or DTPA.

Example 1. Comparison of Q Scores from Samples Prepared Using Different Chelators A comparative study was conducted using a buffer SWS Streptavidin Wash Buffer for nucleic acid sample preparation, where the buffer was modified to remove the EDTA and include DFO-B, EGTA or DTPA in concentrations of 2.0 mM, 1.5 mM, 1.0 mM, 0.5 mM, 0.2 mM, 0.1 mM, 0.05 mM, or 0.0 mM (EWS_noEDTA). The unmodified buffer containing 0.2 mM EDTA was included as a control (EWS_Control). Following sample preparation, the samples were sequenced using HiSeq 2500 sequencing protocol, in standard reagents, and the Q scores were calculated. The Q scores for the individual samples show a distinct and significant increase in maximum quality of the basecalls due to reduction in oxidation and C to A transversion (FIG. 1). Elimination of EDTA from the sample led to a significant increase in Q score, with the inclusion of DFO-B resulting in further improvement. Substitution of EGTA or DTPA for EDTA also resulted in improved Q score.

The result shows that DFO-B mesylate salt, a bacterial siderophore, overcomes the oxidative damage to DNA during the biochemical library prep process due to its ability to chelate FeIII. Further advantages afforded by DFO-B are based on the agent's ability to react directly with free radicals formed under certain conditions in solution. Free radicals can also damage DNA leading to loss of integrity of samples prepared for sequencing.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of embodiments of the invention.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention. Additionally, although the invention is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the invention, whether or not such embodiments are described, and whether or not such features are presented as being a part of a described embodiment. Thus the breadth and scope of the invention should not be limited by any of the above-described exemplary embodiments.

All publications, including patent documents and scientific articles, referred to in this application and the bibliography and attachments are incorporated by reference for the referenced materials and in their entireties for all purposes to the same extent as if each individual publication were individually incorporated by reference.

Citation of the above publications or documents is not intended as an admission that any of the foregoing is pertinent prior art, nor does it constitute any admission as to the contents or date of these publications or documents.

What is claimed is:

1. A method for sequencing a nucleic acid library, which comprises:
   providing a plurality of nucleic acid molecules from a sample;
   generating a nucleic acid library by manipulating the plurality of nucleic acid molecules in a reagent for nucleic acid preparation comprising a siderophore, wherein the manipulating is performed in the absence of ethylene diamide tetraacetic acid (EDTA); and
   sequencing the nucleic acid library to determine a plurality of nucleic acid sequences, wherein the plurality of nucleic acid sequences have an increased Q score compared to a Q score for a plurality of nucleic acids sequences determined from a nucleic acid library that has been generated in the absence of the siderophore.

2. The method of claim 1, wherein said manipulating the plurality of nucleic acid molecules comprises hybridizing the plurality of nucleic acid molecules to a plurality of oligonucleotide probes.

3. The method of claim 2, wherein the plurality of nucleic acid molecules and/or the plurality of oligonucleotide probes are immobilized on a support.

4. The method of claim 3, wherein the plurality of nucleic acid molecules and/or the plurality of oligonucleotide probes are immobilized on the support through a binding partner pair.

5. The method of claim 3, wherein the support is a magnetic bead.

6. The method of claim 2, comprising modifying the oligonucleotide probes specifically bound to the plurality of nucleic acid molecules.

7. The method of claim 1, comprising fragmenting the plurality of nucleic acid molecules.

8. The method of claim 1, comprising adding adapters to the plurality of nucleic acid molecules.

9. A method for sequencing a nucleic acid molecule, comprising:
   preparing the nucleic acid molecule in the absence of ethylene diamide tetraacetic acid (EDTA); and
   sequencing the nucleic acid to determine a nucleic acid sequence, wherein the nucleic acid sequence has a Q score greater than a Q score for a nucleic acid sequence determined from a nucleic acid molecule that has been prepared in the presence of EDTA.

10. The method of claim 9, wherein said preparing the nucleic acid molecule comprises preparing the nucleic acid molecule in the presence of a siderophore.

11. The method of claim 10, wherein the siderophore is a bacterial siderophore.

12. The method of claim 10, wherein the siderophore is a desferrioxamine B (DFO-B) mesylate salt.

13. The method of claim 10, wherein the siderophore has a concentration of 0.01 mM to 1 mM.

14. The method of claim 9, wherein said preparing the nucleic acid molecule comprises exposing the nucleic acid molecule to Fe(III).

15. The method of claim 9, wherein said preparing the nucleic acid molecule comprises exposing the nucleic acid molecule to a magnetic bead.

16. The method of claim 9, wherein said method reduces oxidative damage comprising a point mutation in the nucleic acid molecule.

17. The method of claim 16, wherein the point mutation is a C to A transversion.

18. The method of claim 9, further comprising determining the Q score for the nucleic acid sequence determined from the polynucleotide prepared in the absence of EDTA.

19. The method of claim 1, further comprising determining the Q score for the plurality of nucleic acids sequences determined from the nucleic acid library that has been generated in the reagent comprising the siderophore.

20. The method of claim 1, wherein the siderophore has a concentration of 0.01 mM to 1 mM.

* * * * *

UNITED STATES PATENT AND TRADEMARK OFFICE
CERTIFICATE OF CORRECTION

PATENT NO. : 10,724,075 B2
APPLICATION NO. : 15/787968
DATED : July 28, 2020
INVENTOR(S) : Vincent Peter Smith et al.

It is certified that error appears in the above-identified patent and that said Letters Patent is hereby corrected as shown below:

In the Drawings

In sheet 1 of 1, FIG. 1, X-axis, Line 1 (approx.), delete "Desferroxiamine" and insert --Desferrioxamine--.

In sheet 1 of 1, FIG. 1, X-axis, Line 1 (approx.), delete "Desferroxiamine" and insert --Desferrioxamine--.

In sheet 1 of 1, FIG. 1, X-axis, Line 1 (approx.), delete "Desferroxiamine" and insert --Desferrioxamine--.

In sheet 1 of 1, FIG. 1, X-axis, Line 1 (approx.), delete "Desferroxiamine" and insert --Desferrioxamine--.

In sheet 1 of 1, FIG. 1, X-axis, Line 1 (approx.), delete "Desferroxiamine" and insert --Desferrioxamine--.

In sheet 1 of 1, FIG. 1, X-axis, Line 2 (approx.), delete "EWS_nooEDTA" and insert --EWS_noEDTA--.

In the Specification

In Column 3, Line 24, delete "normucleotidic" and insert --non-nucleotide--.

In Column 3, Line 27, delete "as)" and insert --as--.

In Column 3, Line 37, delete "intemucleotide" and insert --internucleotide--.

In Column 4, Line 11, delete "6× SSPE," and insert --6×SSPE,--.

Signed and Sealed this
Twenty-seventh Day of October, 2020

Andrei Iancu
*Director of the United States Patent and Trademark Office*

CERTIFICATE OF CORRECTION (continued)
U.S. Pat. No. 10,724,075 B2

In Column 4, Line 13, delete "polyvinylpyrolidone," and insert --polyvinylpyrrolidone,--.

In Column 4, Line 14, delete "20× SSPE" and insert --20×SSPE--.

In Column 4, Line 15, delete "ethylene diamide tetraacetic" and insert --ethylenediaminetetraacetic--.

In Column 5, Line 30, delete "arthrob actin," and insert --arthrobactin,--.

In Column 5, Line 41, delete "log Kf(FeIII)" and insert --logKf(FeIII)--.

In Column 5, Lines 43-44, delete "log Kf(FeIII)" and insert --logKf(FeIII)--.

In Column 6, Line 36, delete "Nestera®" and insert --Nextera®--.

In Column 6, Line 42, delete "(TC #-PMM)," and insert --(TC#-PMM),--.

In Column 7, Line 15, delete "single stranded" and insert --single-stranded--.

In Column 9, Line 26, delete "P: Q=-10 log10P." and insert --P: Q=-10log10P.--.

In Column 9, Line 47, delete "length(L)" and insert --length (L)--.

In Column 11, Line 2, delete "chemiluminscent" and insert --chemiluminescent--.

In Column 13, Line 38, delete "No." and insert --Nos.--.

In Column 16, Line 27, delete "FeIII." and insert --Fe(III).--.

In the Claims

In Column 17, Line 18, Claim 1, delete "ethylene diamide tetraacetic" and insert --ethylenediaminetetraacetic--.

In Column 17, Line 22, Claim 1, delete "nucleic acids sequences" and insert --nucleic acid sequences--.

In Column 18, Line 6, Claim 9, delete "ethylene diamide tetraacetic" and insert --ethylenediaminetetraacetic--.

In Column 18, Line 36, Claim 19, delete "nucleic acids sequences" and insert --nucleic acid sequences--.